(12) United States Patent
Gautam

(10) Patent No.: US 9,149,344 B2
(45) Date of Patent: Oct. 6, 2015

(54) CUSTOMIZED WIRE DEVICE FOR ORTHODONTIC ALIGNMENT

(71) Applicant: Pawan Gautam, Las Vegas, NV (US)

(72) Inventor: Pawan Gautam, Las Vegas, NV (US)

(*) Notice: Subject to any disclaimer, the term of this patent is extended or adjusted under 35 U.S.C. 154(b) by 0 days.

(21) Appl. No.: 14/269,109

(22) Filed: May 3, 2014

(65) Prior Publication Data

US 2015/0250560 A1  Sep. 10, 2015

Related U.S. Application Data

(62) Division of application No. 14/202,656, filed on Mar. 10, 2014.

(51) Int. Cl.
 *A61C 7/00* (2006.01)
 *A61C 7/30* (2006.01)

(52) U.S. Cl.
 CPC .. *A61C 7/002* (2013.01); *A61C 7/30* (2013.01)

(58) Field of Classification Search
 CPC .......... A61C 7/00; A61C 7/002; A61C 7/026; A61C 7/12; A61C 7/14; A61C 7/145; A61C 7/146; A61C 7/16; A61C 7/20; A61C 7/28
 USPC .......... 433/8–13, 15, 16, 18–20, 24
 See application file for complete search history.

(56) References Cited

U.S. PATENT DOCUMENTS

2008/0248439 A1* 10/2008 Griffith et al. ............. 433/8

* cited by examiner

*Primary Examiner* — Ralph Lewis

(57) ABSTRACT

The appliance of the present invention is a customized wire device for orthodontic alignment of the mal-aligned teeth. The final position and orientation of the brackets are assessed by simulating the desired aligned stage. Once the final position and orientation of the brackets is known from the simulated aligned stage, this bracket position and orientation is preserved by passing a wire passively through these brackets at the desired aligned stage. This passive wire essentially forms a template of final aligned stage; when securely engaged in the brackets on the mal-aligned stage this wire needs to be deflected and generates forces that align the teeth to its designed aligned stage due to elastic recoil of the wire.

13 Claims, 11 Drawing Sheets

← 11

CUSTOMIZED WIRE DEVICE FOR ORTHODONTIC ALIGNMENT

CROSS REFERENCE TO RELATED APPLICATION

This application is related to U.S. Provisional Patent Application Ser. No. 61/776,436 filed, Mar. 11, 2013 and pending U.S. Non Provisional patent application entitled "ORTHODONTIC APPLIANCE" application Ser. No. 14/202,656, filed Mar. 10, 2014, which is incorporated herein by reference in its entirety.

FIELD OF THE INVENTION

The present invention is generally related to orthodontic appliances. More particularly, the invention relates to an orthodontic archwire that is customized for alignment of patient's teeth and can be attached to bracket affixed to the mal-aligned teeth, to bring the mail-aligned teeth into a rapid three dimensional alignment with minimum friction.

BACKGROUND OF THE INVENTION

Mal-aligned teeth detract from the aesthetic appeal of a smile and impart a negative image of the wearer of the smile. Therefore, straightening and aligning mal-aligned teeth has gained in popularity over the years. Correcting mal-aligned teeth is the exclusive domain of orthodontists who use various implements and procedures to align a patient's teeth. The underlying principle in aligning mal-aligned teeth involves forcing movement of the mal-aligned teeth from their designated positions and re-positioning them to align with the rest of the teeth. To accomplish this method of orthodontic tooth movement, orthodontists use different appliances. The most commonly used orthodontic appliance is the edgewise appliance and its variation, namely the straight wire appliance.

The edgewise appliance system uses a combination of many individual pieces designed to function in a coordinated fashion. The two primary components of this system are, 1) tooth attachments in the form of brackets and bands, and 2) arch wires that engage the brackets and bands. These attachments which are semi-permanently and rigidly attached to the teeth serve as a handle by which force generated by the wires may be transmitted to the teeth to accomplish orthodontic tooth movement. Each attachment in this system is comprised of an orthodontic bracket bonded to the teeth with adhesives and having a rectangular slot that is capable of receiving and accommodating an arch wire with a round, rectangular or square cross section. The arch wires are held within the bracket slot using ligature ties and are a removable component of the system. During treatment, the orthodontist removes the arch wire and makes adjustments to the same wire or inserts new wires in the bracket slot. The optimum three dimensional movement of the tooth is accomplished when the rectangular slot of the bracket is completely or nearly completely filled by a rectangular arch wire. Even with the rectangular arch wire completely filling the rectangular slot of the bracket, all three degrees of control or movement of the teeth may not be efficient due to the bracket-wire play which is essentially brought about by the difference in size of the bracket slot and the arch wire engaged in that slot. Typically, elastic deflection of the arch wire generates forces that are transmitted to the teeth by the brackets attached to the teeth, thereby causing the teeth to move to a desired position. The degree of elastic deflection of the arch wire in turn depends on the properties of the material used in the construction of the wire and the size, shape and cross section of the arch wire.

In a straight wire appliance system, the angulations and inclinations of the teeth are built into the bracket eliminating the need for bending the arch wires to accomplish tooth movement. In theory, the brackets are rigidly fixed to the teeth at their precise pre-programmed or pre-adjusted positions on the mid-facial or lingual aspect of the teeth at their respective mal-aligned positions. The straight, flat, wire is then deflected to engage the bracket slots. The force generated by the elastic deformation of the wire then pulls the teeth along with it as it moves to its original shape, thereby aligning the teeth. Due to the inherent structural differences in tooth size and shape, while the general shape of the bracket may be very similar, for each particular tooth type the corresponding bracket is designed with specific compensation in the base shape, base size, general shape, slot angulations, base thickness etc, to accommodate for differences in tooth shape, size and its spatial relation relative to the horizontal plane.

Initial stages of the orthodontic treatment are accomplished using small size round wires. Although a relatively thinner wire having a round cross-section does not allow application of torquing (labio-lingual inclination of tooth) forces when engaged within an arch wire slot, it does provide a greater degree of flexibility and generally applies less force in use, which is more comfortable for the patient. The characteristic low force of round arch wires is due to their thinner cross-section. As such, wires having a round cross-section are often useful during the beginning stages of orthodontic treatment when the teeth are most mal-aligned. Use of a round arch wire allows for movement of teeth to correct mainly angulations and rotation with relatively light and therefore more comfortable forces. In this phase, the wire is loosely held in the bracket slot to allow sliding of the wire with minimal friction so that the brackets and the teeth attached to them are moved into alignment. A form of brackets called self-legating brackets have been claimed to perform better in this phase due to passive ligation and minimal forces exerted on the wire, consequently resulting in low friction. Once these corrections have been achieved, a relatively thicker square or rectangular wire typically replaces the round arch wire so as to allow torquing of selected teeth to accomplish labio-lingual inclination of the teeth. Torquing is the most difficult tooth movement to accomplish due to small moment arm. Torquing requires use of thicker and stiffer rectangular wires that engage the bracket slot completely (to avoid play). The use of such wires generates heavy forces that have been documented to cause undesirable side effects like orthodontic root resorption.

The conventional orthodontic treatment systems thus described are a cumbersome process and the bracket-wire interaction during the treatment lacks complete three dimensional control, especially in the initial stages of orthodontic treatment. The customized wire device of the present invention allows a true three dimensional movement of the teeth, bringing them into alignment during the entire orthodontic treatment period because all movements occur simultaneously to move the teeth from their initial mal-aligned stage to the final aligned stage thereby shortening the treatment time, as opposed to conventional orthodontic treatments where a three dimensional control is achieved only in the later stages of the treatment.

SUMMARY OF THE INVENTION

The present invention is a new method of designing a customized wire device that when affixed to the bracket attached to the tooth facilitates movement of the mal-aligned teeth to bring them into rapid three dimensional alignment, with the least friction. The appliance is designed to be facilitate tooth alignment with least friction as the customized wire is not meant to slide as normally occurs with conventional bracket wire interaction. Some embodiments of the appliance can be customized to be used on either labial or lingual tooth surface In the preferred embodiment of the customized wire device of the present invention, the cross section of the wire may be square or rectangular in shape and in other embodiments, the cross section of the wire may be round or polygon-shaped with three or more sides or vary in cross-sections in different sections. In addition, the customized wire may comprise multiple segments and can be single or multi-stranded.

In the preferred embodiment of the customized wire device of the present invention, the wire is made of a polymer material. In other embodiments, the customized wire is formed using a shape memory alloy (SMA) such as, nickel-titanium alloy. In general, the customized wires made of SMA's regain their shape which helps to move the teeth to the desired aligned arrangement. Other embodiments may have the customized wire made of memory polymer material which conforms to the shape of the desired alignment arrangement of the teeth. Other materials used for manufacturing the customized wire include, but are not limited to, rubbers, shape memory rubbers chromium-nickel alloys, cobalt-chromium-nickel-molybdenum, titanium molybdenum-aluminum and stainless steel.

In this summary of the invention, and in the specification in general, the various references to, "an exemplary embodiment," "preferred embodiment," "yet other embodiments" and "some embodiments" do not necessarily refer to the same embodiment(s). Rather, these references to the various embodiments mean that a particular feature, structure, or characteristic described in conjunction with an embodiment is included in at least some embodiments, but not necessarily all embodiments of the invention. Although the present invention has thus been described with reference to its exemplary and related embodiments, these embodiments should not be construed as limitations on the scope of the invention. It is to be understood by those skilled in the art, that the invention can be implemented in embodiments other than the ones described in this summary of the invention.

The objects, embodiments and features of the present invention as described in this summary of the invention will be further appreciated and will become obvious to one skilled in the art when viewed in conjunction with the accompanying drawings, detailed description of the invention, and the appended claims.

DETAILED DESCRIPTION OF THE INVENTION

The appliance of the present invention is a customized wire device for orthodontic alignment of the mal-aligned teeth. In the exemplary embodiment of the invention, the customized wire device has a configuration that is derived from characteristics of both the mal-aligned and aligned states of the teeth. This customized wire device when affixed to the brackets on the teeth results in the rapid alignment of the teeth with minimal friction.

Figure 1:
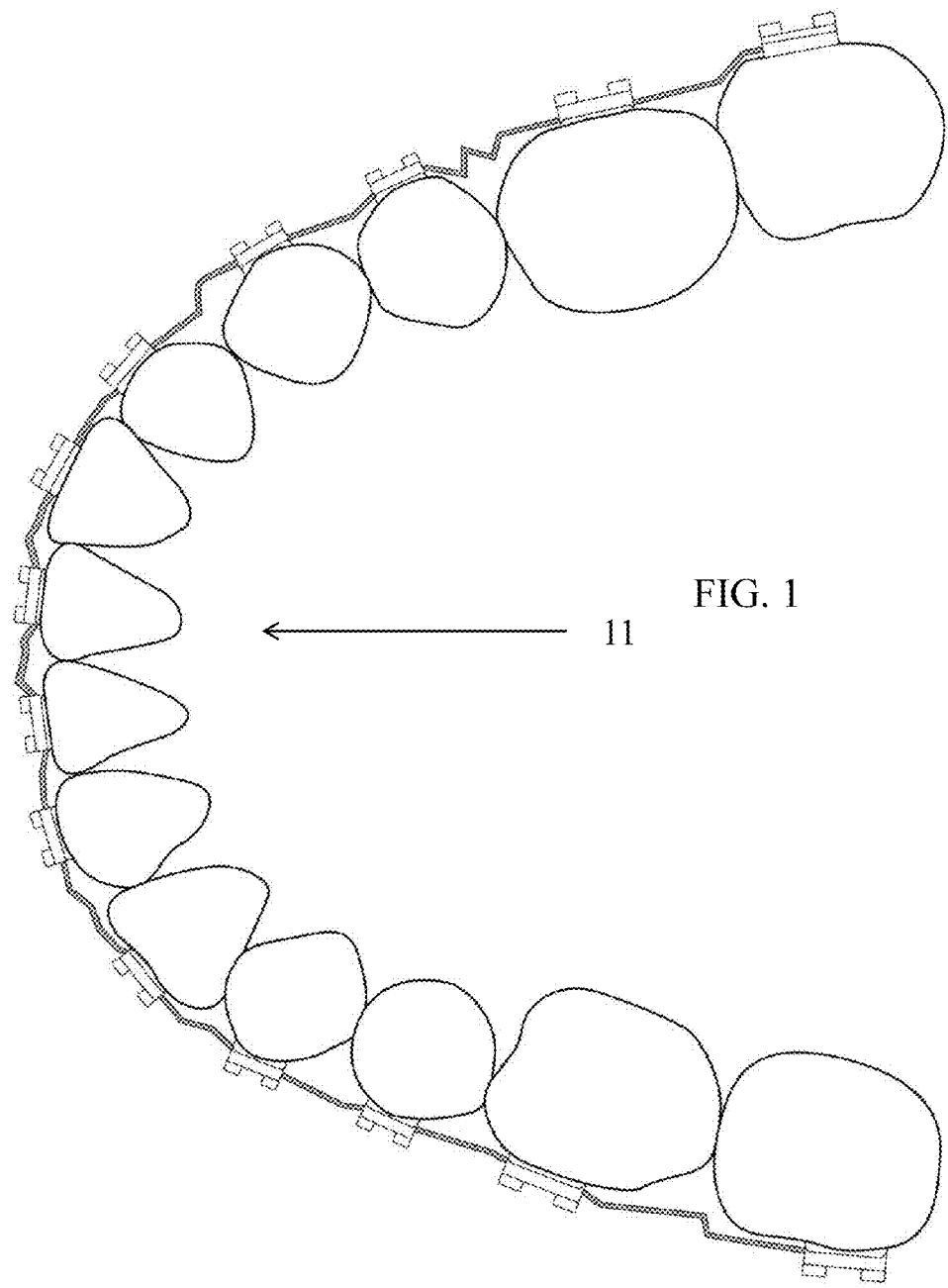
FIG. 1 is a perspective view of the aligned teeth in the patient's mouth with the use of the customized wire device of the present invention.

Referring now to the drawings, in particular, to FIG. 1 a perspective view 11 of the alignment of a set of teeth using the exemplary embodiment of the customized wire device 10 of the present invention is shown. The customized wire device 10 is attached to the bracket 20 that is glued to the surface of the teeth. In this embodiment of the use of the customized wire device 10 of the invention, the initial step is the development of the physical or computerized three dimensional models of the mal-aligned teeth of the patient. Using the physical or electronic three dimensional models thus developed, the bracket is attached to the mal-aligned teeth and a desired aligned arrangement model is developed by simulating various desirable tooth movements. A final geometric form of the desired aligned arrangement arch form is simulated for use. The software or physical measuring device used in the process can be further used to calculate each inter-bracket distance of the mal-aligned arrangement and the desired aligned arrangement. The entire orthodontic treatment by the present invention can be divided into stages and may involve multiple intermediate stages to achieve the final desired alignment stage and the use of a series of customized wire device 10 attached to the bracket 20.

Figure 2:
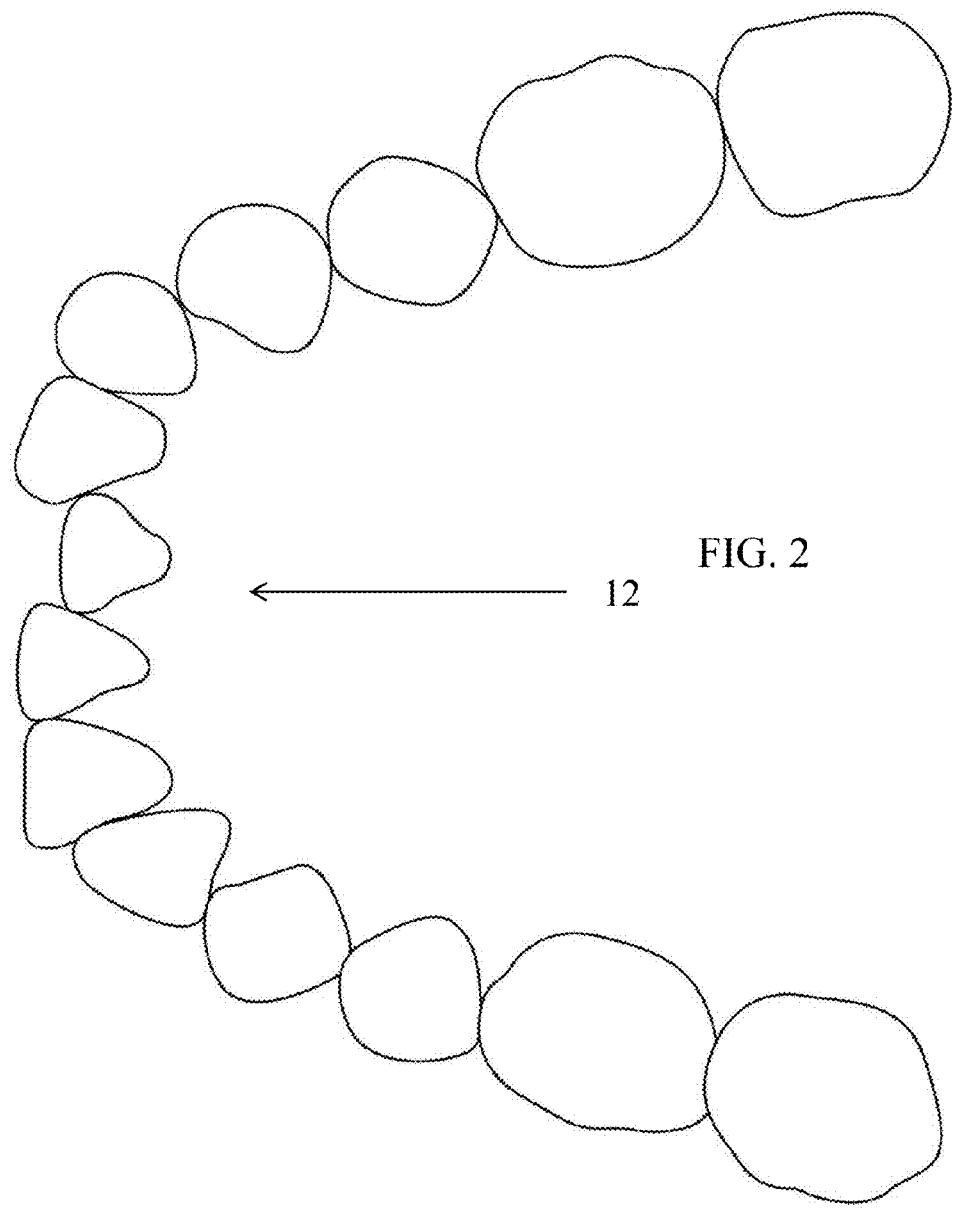
FIG. 2 is a perspective view of a physical or electronic model of the patient's mal-aligned set of teeth.

FIG. 2 is a perspective view 12 of a mal-aligned set of teeth of the patient's physical or electronic model. The physical model of the patient's teeth may be made out of plaster or dental stone or other materials used for this purpose. The electronic model of patient's teeth can be obtained by three dimensional scanning of the impression of patient's teeth or physical model of the teeth and converting them into digital or electronic model using CAD/CAM software.

Figure 3:
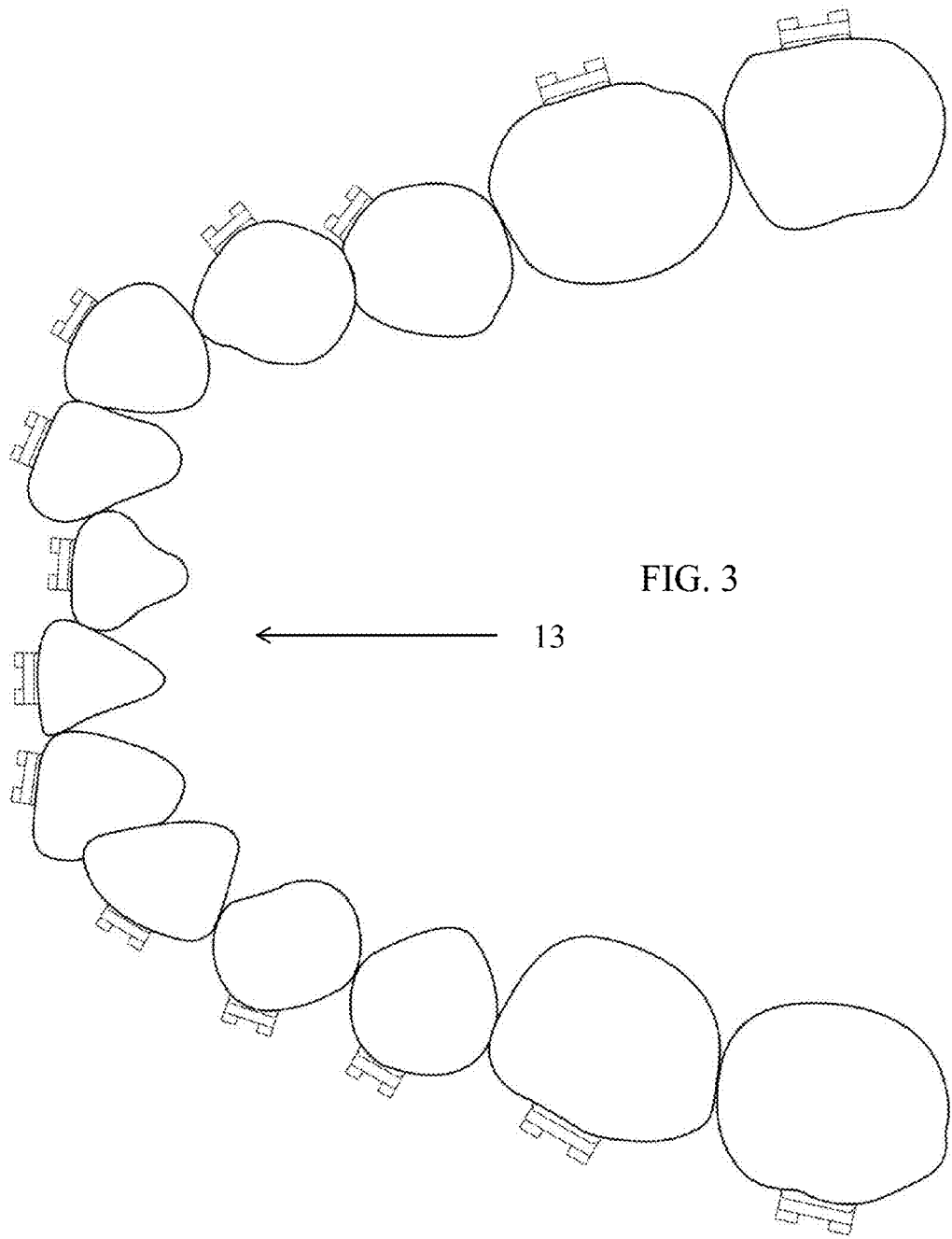
FIG. 3 is a perspective view of the bracket attached to the physical or electronic model of the patient's mal-aligned set of teeth.

FIG. 3 is a perspective view 13 of a set of mal-aligned teeth with the brackets 20 attached to the teeth surface at their desired location and orientation in the physical or electronic model in the patient's mouth.

Figure 4:
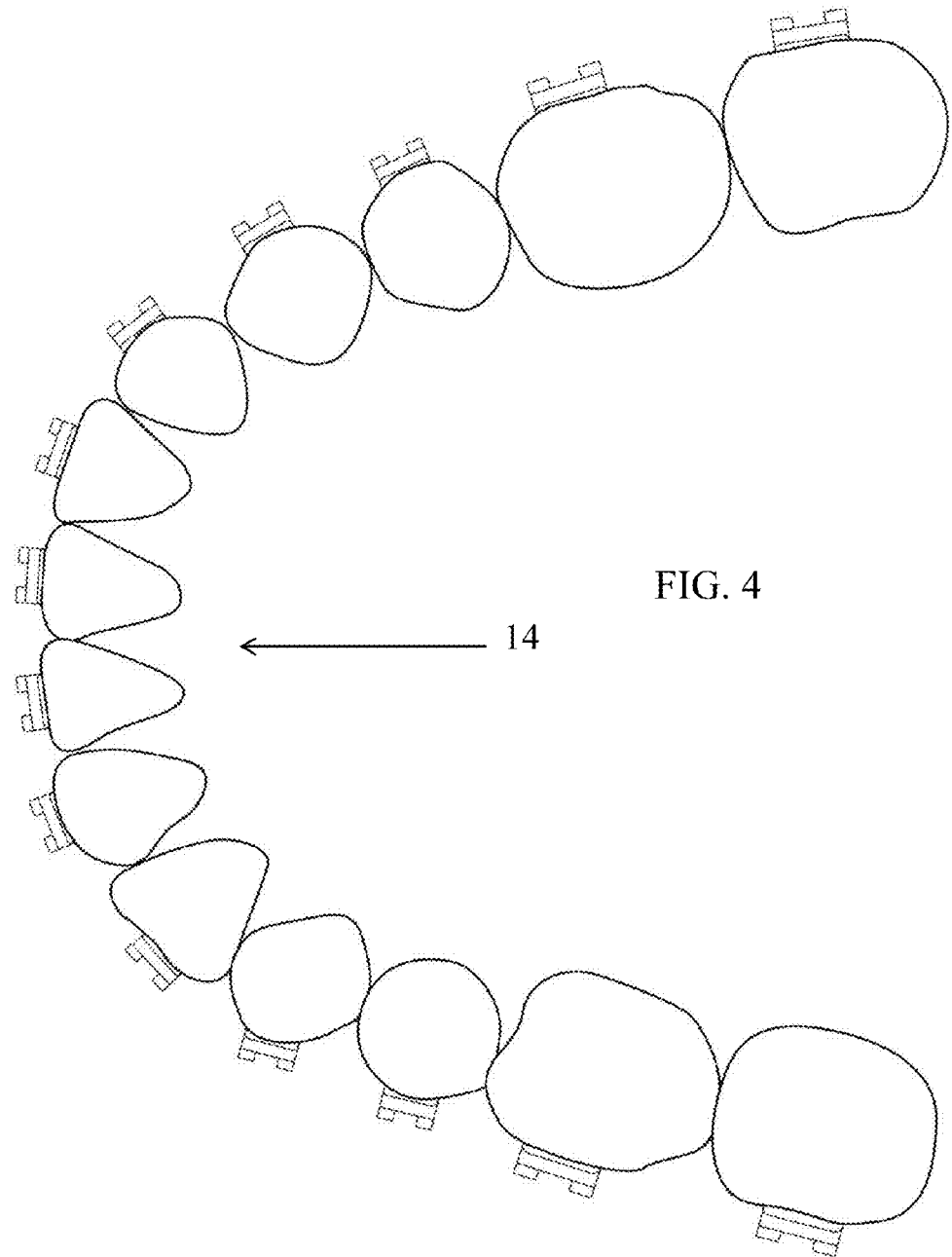
FIG. 4 is a perspective view of the physically or electronically simulated aligned set of the patient's teeth with bracket assembly affixed to the teeth.

FIG. 4 is a perspective view 14 of the physically or electronically simulated aligned set of the patient's teeth with brackets affixed to the teeth. The teeth in the physical or electronic model are simulated to move in their desired alignment. The simulation of alignment involves movement of the teeth, including rotation and translation in all three dimensions, to achieve their desired alignment.

Figure 5:
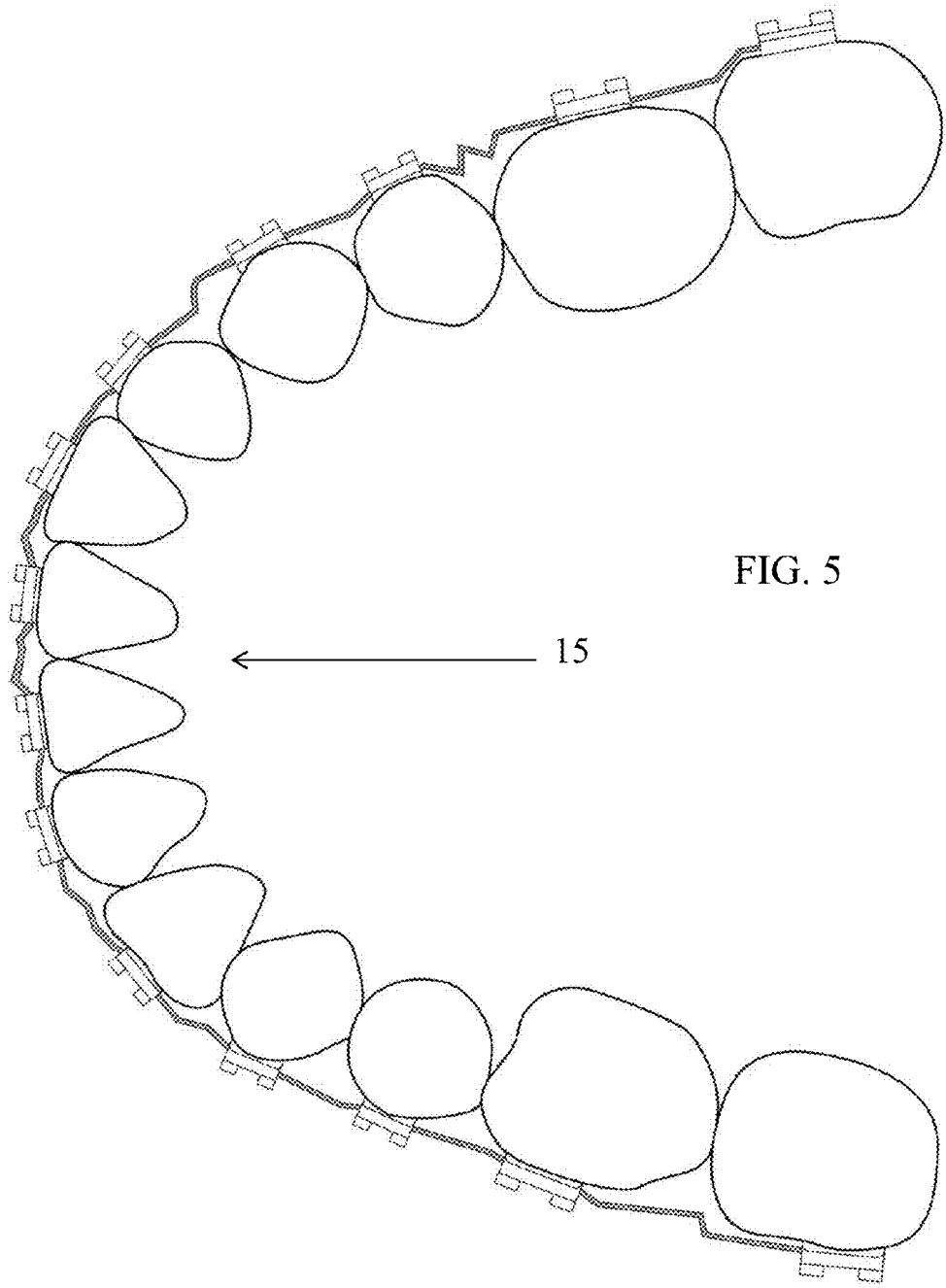
FIG. 5 is a perspective view of the customized wire device of the present invention passing passively through the wire the bracket with physical or electronic model of the patient's teeth in a simulated aligned set.

FIG. 5 is a perspective view 15 of the customized wire device of the present invention passing passively through the bracket with physical or electronic model of the patient's teeth in a simulated aligned set. In this view, the customized wire device 10 of the present invention is seen passing passively through the bracket 20 with physical or electronic model of the patient's teeth in a simulated aligned set. This can be accomplished by incorporating multi-dimensional bends in the wire.

Figure 6:
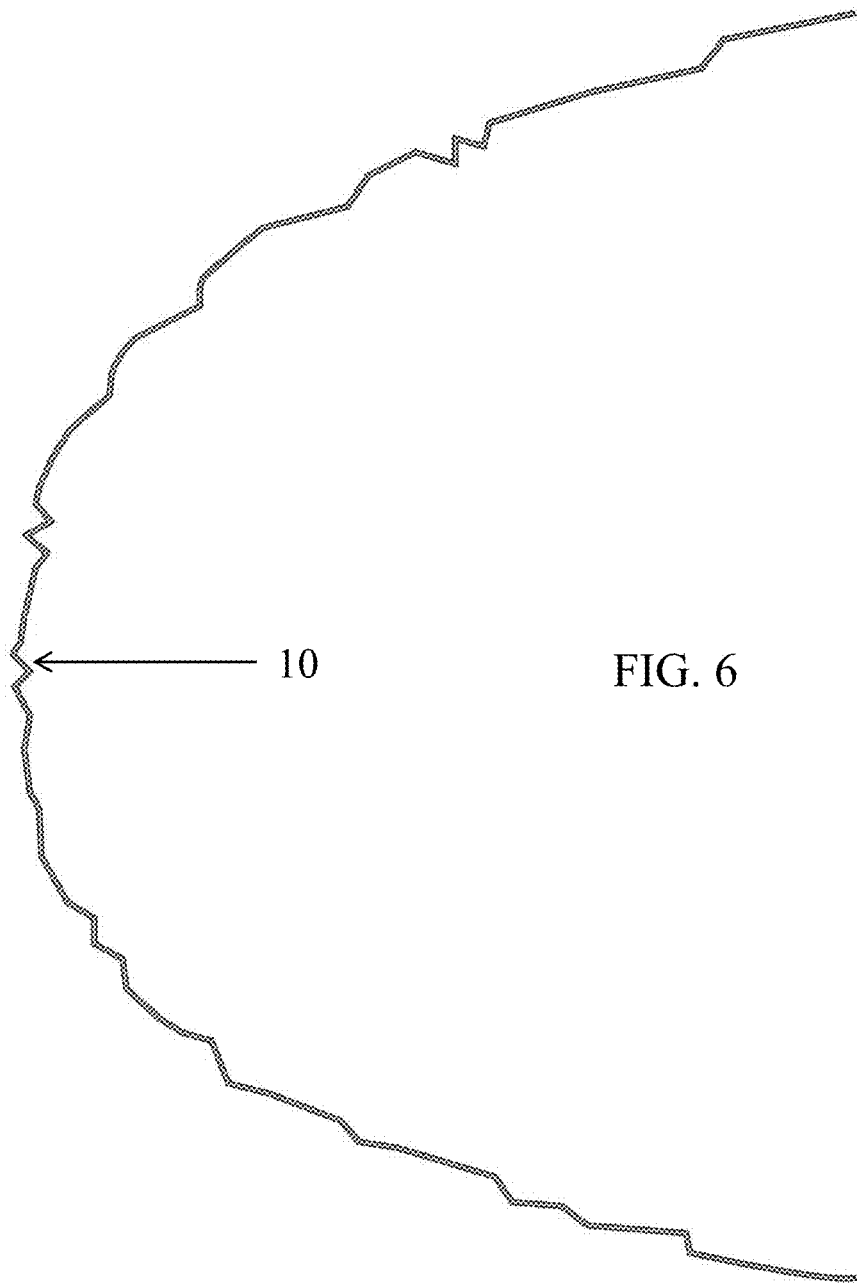
FIG. 6 is a perspective view of the customized wire device.

FIG. 6 is a perspective view of the customized wire device. The customized wire device 10 as seen in this view has multi-dimensional custom bends such that the customized wire device passes passively through the wire slot of the bracket 20. The final position and orientation of the brackets are assessed by simulating the desired aligned stage. Once the final position and orientation of the brackets is known from the simulated aligned stage, this bracket position and orientation is preserved by passing a wire passively through these brackets at the desired aligned stage. To achieve the passive state of wire through these brackets, the wire may have one or more multi-dimensional bends. This passive wire essentially forms a template of final aligned stage and when securely engaged in the brackets (such that there in minimum wire-bracket sliding or rotation of the wire within the bracket) on the mal-aligned stage will align the teeth to its designed aligned stage due to elastic recoil of the wire. Once this arrangement of the customized wire device 10 within the slot of the bracket is achieved, the customized wire device 10 is attached to the bracket 20 so that there is limited sliding or no sliding at all back and forth, or rotation of the wire in the wire slot of the wire component 20. In the preferred embodiment of the customized wire device 10 the wire is made of a polymer material and is square or rectangular in shape. In other embodiments the customized wire device 10 may be round or polygon-shaped with three or more sides and may also comprise multiple segments and can be constructed using various materials including shape memory polymers, rubbers, shape memory rubbers, shape memory alloys and other such materials.

The customized wire device 10 and its related system have the following features: Wire length: Determined by the n bracket widths, where n is the number of teeth that will have bracket assembly attached to them and n−1 inter-bracket distances. The bracket widths are constant for specific teeth. Each inter-bracket distance for the wire component will be determined from the corresponding inter-bracket distance of the mal-aligned arrangement model of the teeth and the desired aligned arrangement model for the teeth whichever is greater. Therefore the length of this wire component will be n bracket width+n−1 inter-bracket distances. In each inter-bracket space where mal-aligned arrangement inter-bracket width is greater than desired aligned arrangement inter-bracket distance, curves, bends and/or loops can be incorporated in that specific inter-bracket space such that the distance between the adjacent wire components is smaller than the length of the wire between the adjacent wire components when the customized wire device 10 is in passive state before the incorporation of curves, bends and/or loops corresponds to the mal-aligned arrangement inter-bracket distance and the wire length after curves, bends and/or loops equals or is less than the desired aligned arrangement inter-bracket distance. Such an arrangement facilitates attachment of the wire component to the tooth component at the mal-aligned stage. On the other hand, incorporation of curves bends and loops in that inter-bracket span facilitates movement of teeth into desired alignment due to elastic recoil of the wire, Wire Arch form: Corresponds to the desired aligned arrangement arch form of the patient. This in turn includes geometric form or V, U or any other shape. The desired aligned arrangement serves as a template for the customized wire device such that the orthodontic archwire 10 fits over the brackets 20 affixed to the desired aligned arrangement model. Multi-dimensional bends: The customized wire device 10 may also have multi-dimensional bends as seen in FIG. 6 such that the wire passes passively through the wire slot of the bracket 20 when each bracket 20 is attached to the corresponding tooth at the desired aligned stage.

Figure 7:
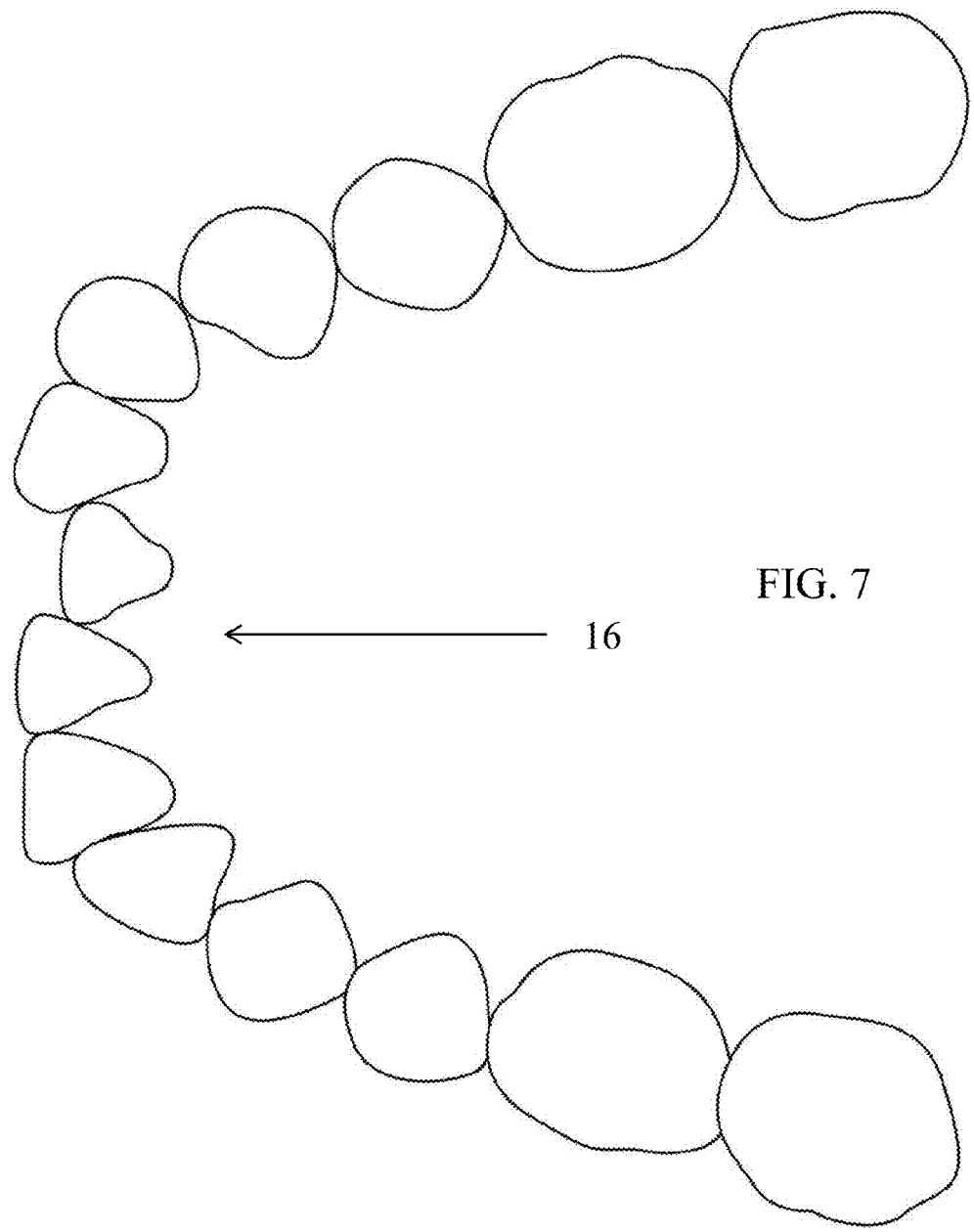
FIG. 7 is a perspective view of a mal-aligned set of teeth in the patient's mouth

FIG. 7 is a perspective view 16 of a mal-aligned set of teeth in the patient's mouth. The mal-alignment of teeth involves rotation and bodily displacement of teeth from ideal position.

Figure 8:
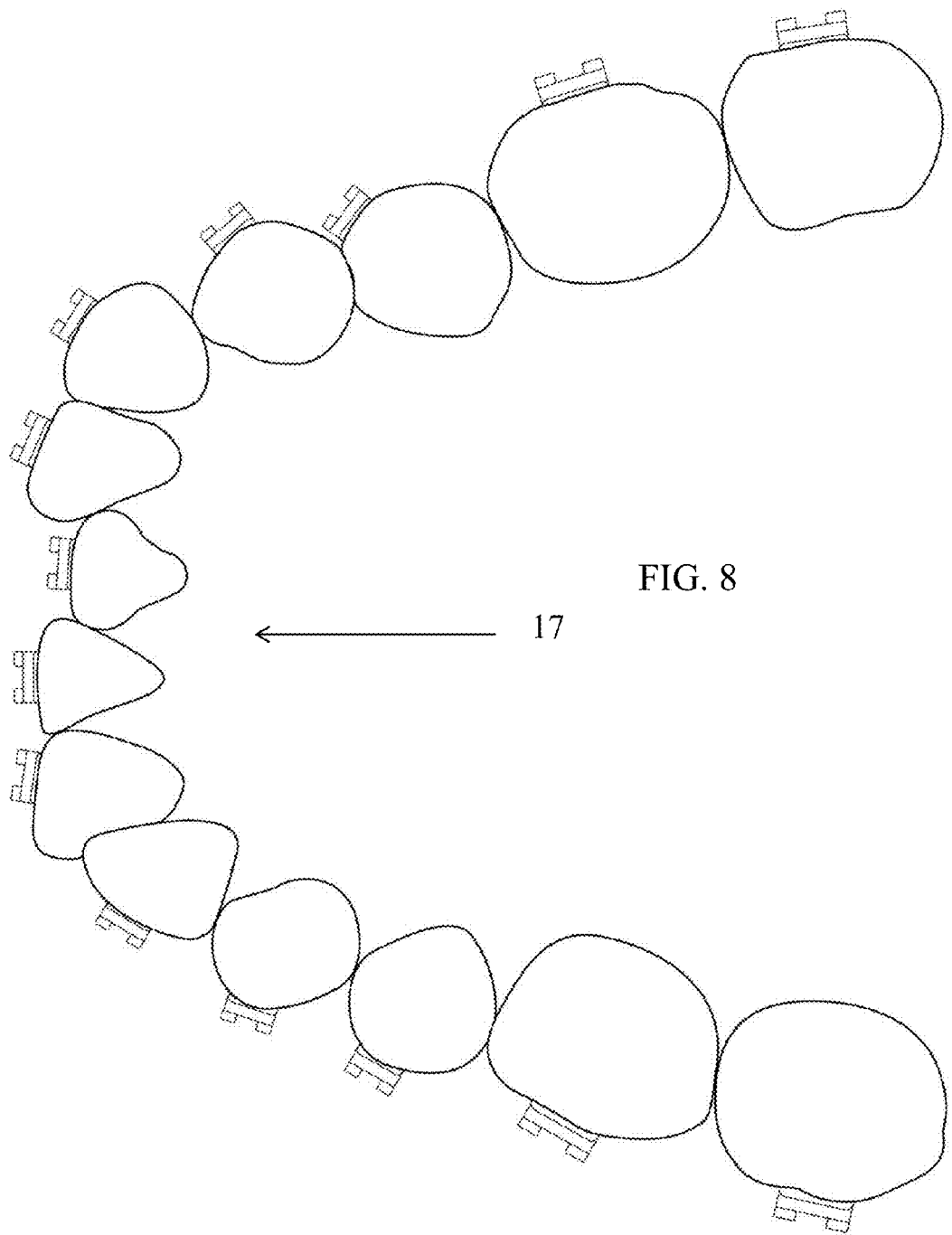
FIG. 8 is a perspective view of a mal-aligned set of teeth in the patient's mouth with bracket transferred from the physical and electronic model of the patient's teeth to the patient's teeth in the mouth and affixed at the same position and orientation as in FIG. 3.

FIG. 8 is a perspective view 17 of a mal-aligned set of teeth in the patient's mouth with the bracket 20 affixed to the mal-aligned teeth. In this view, the bracket 20 can be seen affixed to the tooth surface. The brackets are transferred to the patient's mouth using indirect bonding technique, as described earlier. The brackets are attached to the tooth surface by a procedure commonly referred to as bonding. Of the two commonly used bonding procedures, direct bonding and indirect bonding, the indirect bonding procedure is used in the preferred embodiment preferably used for accuracy in bracket positioning over the patient's teeth. In this procedure, the brackets are positioned on the three dimensional model of the patient's teeth, outside the patient's mouth. Once the brackets are positioned and attached to the model, a transfer tray is fabricated preserving the position of the brackets relative to the teeth. In the preferred embodiment of the present invention, a physical model of the patient's mal-aligned teeth arrangement is first constructed in order to fabricate the indirect bonding tray. The brackets will be attached to the facial or lingual surface at the desired location and desired orientation on the tooth surface. The transfer tray is constructed using a putty or flexible plastic material that is pressed over the model and the bracket such that it covers at least the occlusal/incisal and the surface where the tooth component needs to be attached. The transfer tray is removed making sure that the brackets are now embedded in the transfer tray. This transfer tray will have the shape of a patient's dental anatomy with the bracket 20 releasably attached to the transfer tray. In order to bond the bracket 20 to the teeth, the teeth are prepared by etching, priming and coating their surfaces with adhesive. The transfer tray is then placed in the patient's mouth and pressed over the patient's teeth until the adhesive cures either chemically or using visible light. The tray is then removed from the mouth while the bracket 20 remain firmly bonded to the teeth surfaces at their desired location and orientation as in the physical or electronic model in the patient's mouth.

Figure 9:
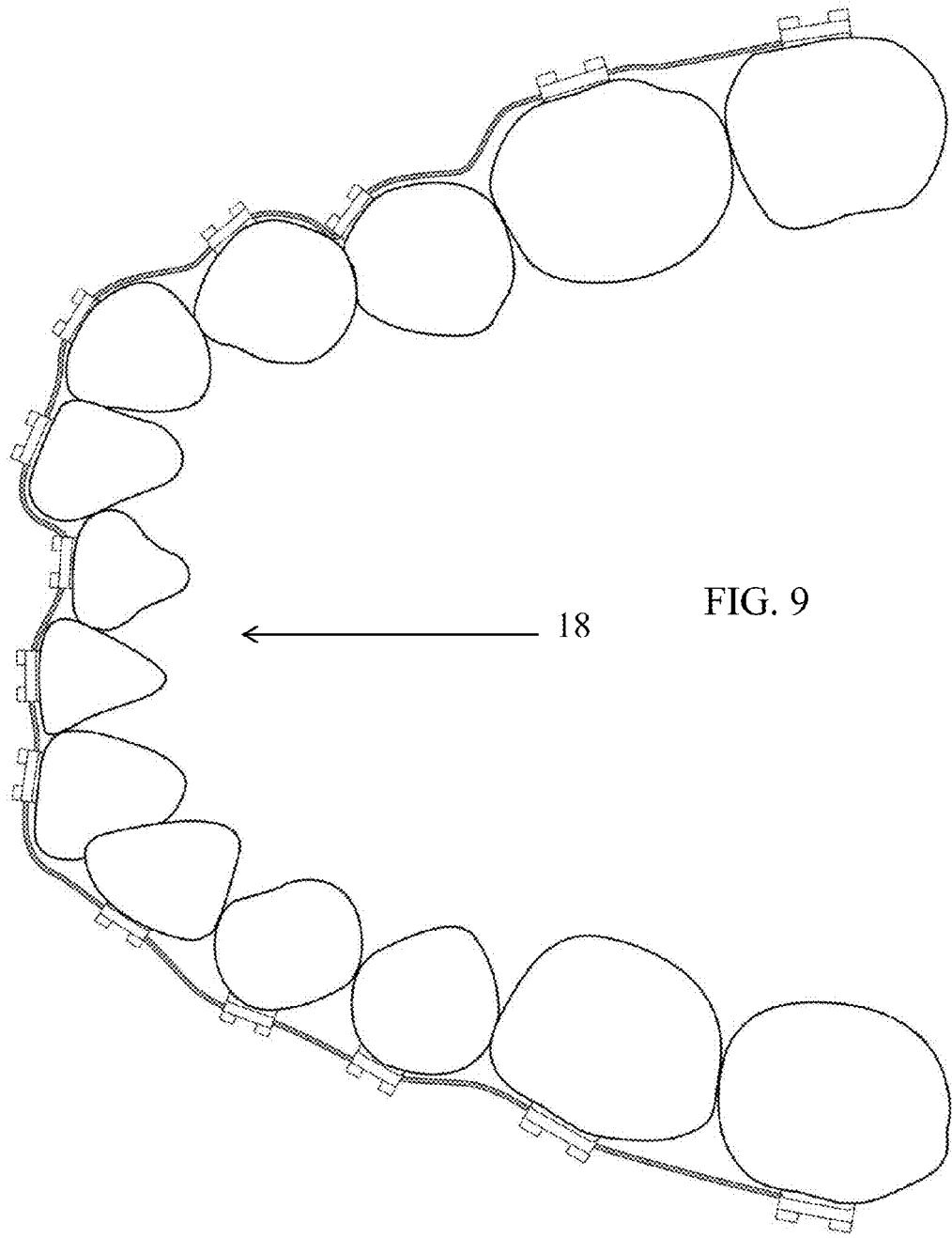
FIG. 9 is a perspective view of the customized wire device of the present invention engaged in the brackets affixed to the teeth in the patient's mouth. The customized wire device can be secured in place with ties, clips or adhesives (not shown here) such that there is minimum relative movement between the wire and the bracket.

FIG. 9 is a perspective view 18 of a set of mal-aligned teeth with the customized wire device 10 attached to the bracket 20 in the patient's mouth. The customized wire device 10 with its appropriate arch form and optimum length is secured in the brackets on the patient's teeth resulting in deflection of the wire and application of forces on the teeth. The customized wire device can be secured in place with ties, clips or adhesives (not shown here) such that there is minimum relative movement between the wire and the bracket.

Figure 10:
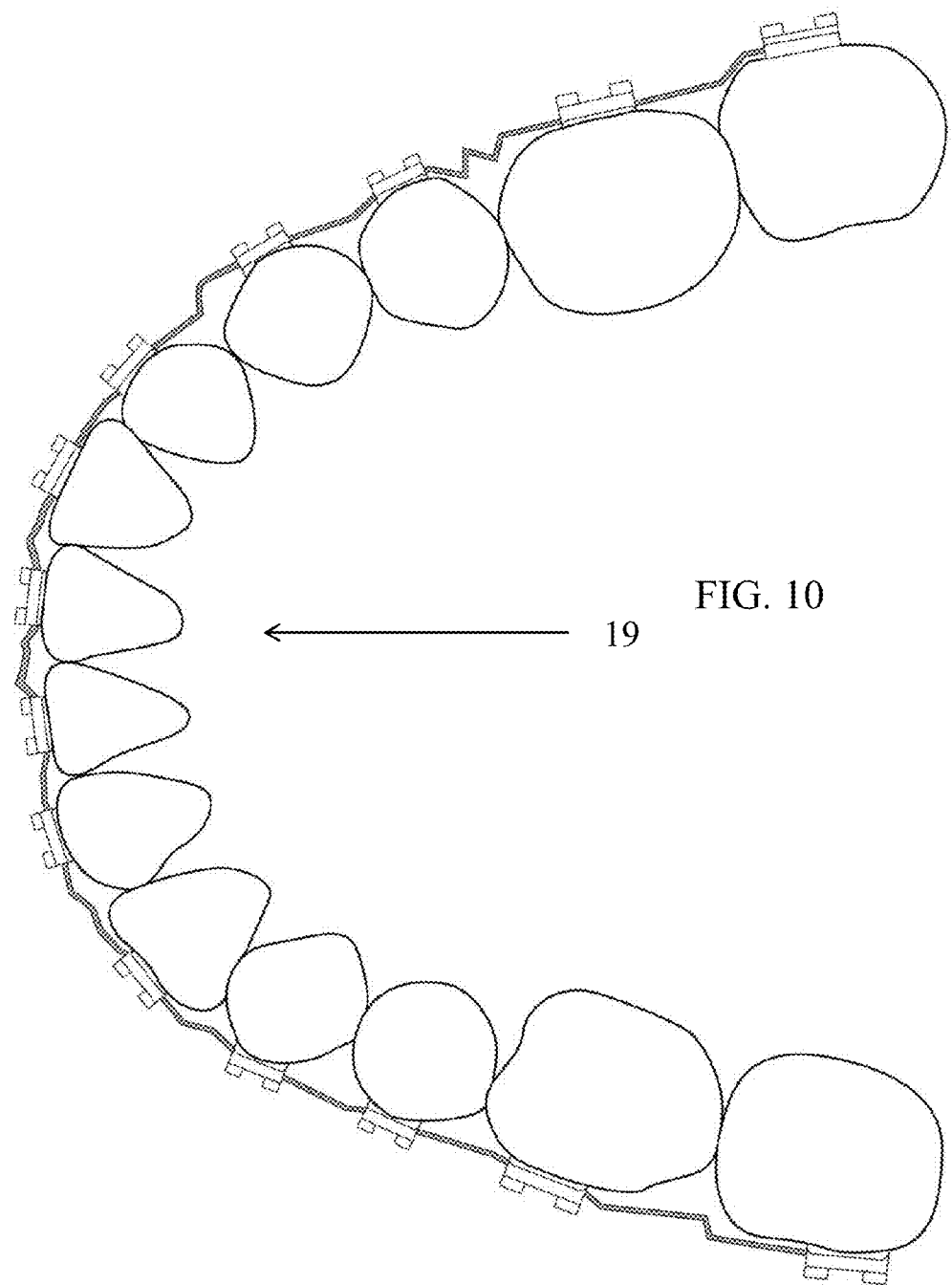
FIG. 10 is a perspective view of the aligned teeth in the patient's mouth with the use of the customized wire device of the present invention.

FIG. 10 is a perspective view 19 of an aligned set of teeth resulting from the use of the customized wire device 10. As described previously, the customized wire device 10 was securely engaged in the bracket 20 such that there is no bracket-wire sliding and the wire does not rotate within the bracket. Securely engaging the customized wire device in the brackets 20 results in elastic deflection of the customized wire device 10 and will apply the necessary forces to move the teeth to the desired aligned arrangement due to the elastic recoil of the customized wire device 10. A series of customized wire device may be required to achieve the final satisfactory alignment of the teeth. The series of customized wire device are sequentially used to align the dentition in all three dimensions of space. The so called prescription of the bracket is built in as a result of brackets oriented in their ideal position over the model of the desired aligned arrangement. The teeth are brought into desired aligned arrangement as forces are being transmitted to the teeth after the customized wire device 10 is securely attached to the bracket 20.

Figure 11:
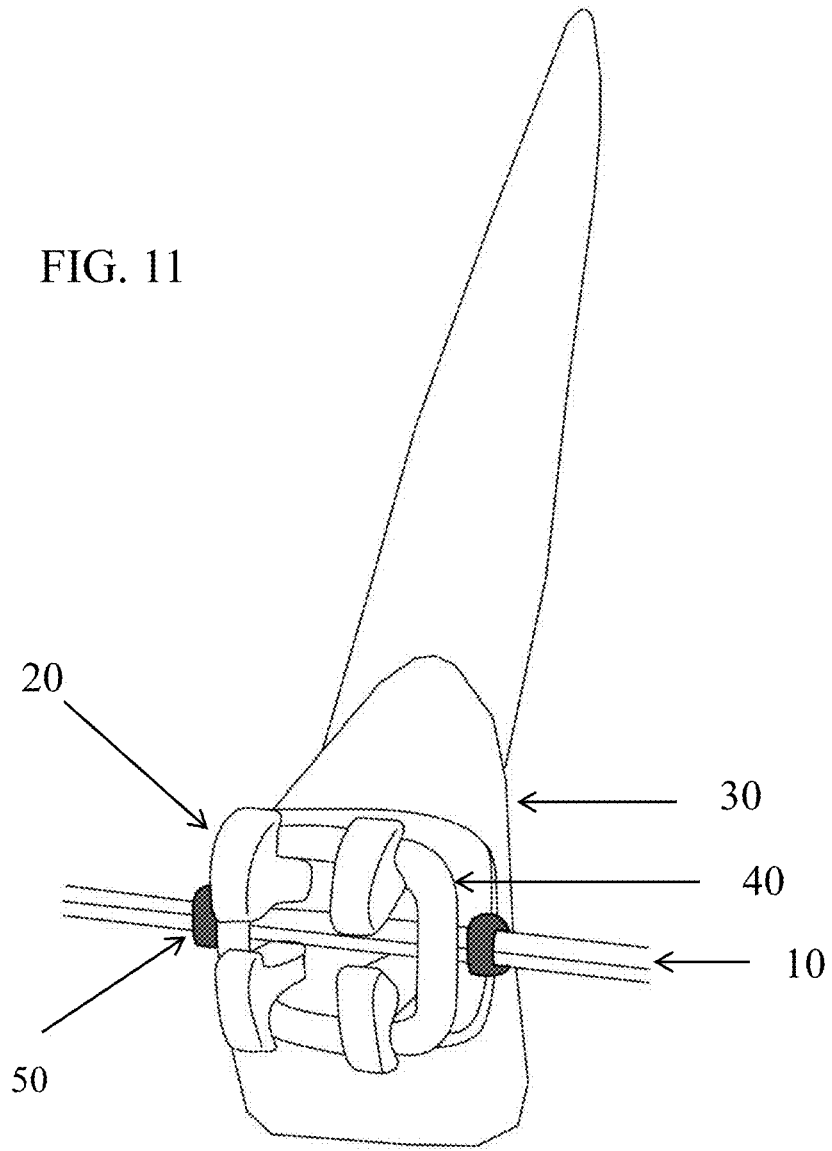
FIG. 11 is a perspective view of the bracket attached to a tooth surface and the mode of attachment of custom wire device to the bracket

FIG. 11 is a perspective view of the bracket attached to a tooth surface and the mode of attachment of custom wire device to the bracket. The bracket 20 is affixed to the tooth surface 30. The customized wire device 10 is held in place within the bracket slot by means of ties 40 that go around the bracket 20 and prevent the wire from sliding out of the bracket slot. In addition, stops 50 can be attached to the wire adjacent to the bracket 20 to prevent the wire from sliding back and forth within the bracket slot. In this preferred embodiment, the customized wire device 10 made of rectangular wire prevents rotation of the customized wire device within the rectangular bracket slot.

The foregoing description of the exemplary embodiments of the present invention through the drawings and the detailed description of the manner of using the customized wire device in the orthodontic appliance system should not be construed to limit the scope of the invention. It is to be understood that the embodiment of the present invention as described herein do not limit any application or scope of the invention and that the invention can be carried out and practiced in various ways and implemented in embodiments other than the one outlined in the description above. It is to be further understood that the phraseology and terminology used to describe the invention are for descriptive purposes only. It should be understood and obvious to one skilled in the art that alternatives, modifications, and variations of the embodiment of the present invention may be construed as being within the spirit and scope of the appended claims.

What is claimed is:

1. A method of producing a customized arch wire device for orthodontic alignment of teeth, said method comprising:
   obtaining a model of a patient's mal-aligned teeth, said model having a plurality of teeth surfaces;
   attaching a plurality of brackets to said teeth surfaces, each bracket having a width and a wire slot to accommodate said arch wire;
   wherein adjacent brackets are spaced apart by a plurality of inter-bracket distances;
   determining how said brackets move from their mal-aligned position to their aligned position in a simulated desired aligned stage of said patient's teeth;
   obtaining an arch wire device comprising a customized wire length;
   outside a patient's mouth, positioning said customized arch wire device into a geometric form that corresponds to the position and orientation of said plurality of brackets on said teeth surfaces in said simulated desired aligned stage;
   wherein said customized arch wire device's length is comprised of a combined width of said brackets and combined inter-bracket distances between each set of adjacent brackets;
   wherein said customized arch wire device further comprises multi-dimensional bends such that said customized arch wire device passes passively through each bracket affixed to said teeth surfaces of said simulated desired aligned stage; and
   wherein said multi-dimensional bends are further configured so that when a corresponding plurality of brackets are affixed in said patient's mouth at the same position and orientation as in said model, and said customized arch wire device is secured in place in said wire slots of said plurality of brackets with ties, clips, stops, adhesive or a combination of these, there is minimal movement between said customized arch wire device and said plurality of brackets.

2. The method as described in claim 1, wherein each said inter-bracket distance is configured to be the greater of:
   A) a length of said customized arch wire device between adjacent brackets in said model of said patient's mal-aligned teeth, or
   B) the length of said customized arch wire device between adjacent brackets in said model for a simulated desired aligned stage.

3. The method as described in claim 2, wherein if said inter-bracket distance is smaller in said model for a simulated desired aligned stage than said inter-bracket distance is in said model of said patient's mal-aligned teeth, then;
   further configuring a corresponding portion of said arch wire to consist of curves and bends such that the distance between said brackets, when said arch wire is in a passive or recoiled state, is reduced to the length of said inter-bracket distance for said models for a simulated desired aligned stage.

4. The method as set forth in claim 1 wherein said customized arch wire device is configured to perform tooth alignment using brackets attached to any of labial or lingual tooth surfaces.

5. The method as set forth in claim 1 wherein said customized wire device further comprises any of multi-dimensional bends, curves, rotations or twists to achieve said desired aligned stage of a patient's mal-aligned teeth.

6. The method as set forth in claim 1 wherein said customized arch wire device has a square, rectangular, polygonal or circular cross section.

7. The method as set forth in claim 1 wherein said customized arch wire device is formed from either single stranded or multi-stranded wire.

8. The method as set forth in claim 1 wherein said customized arch wire device is fabricated from plastic, polymers, metals, metal alloys, shape memory polymers, rubbers or a combination of these.

9. The method of claim 1, wherein said arch wire has a cross section that is a polygon with at least three sides.

10. The method of claim 1, wherein said arch wire is configured to be capable being completely detachable and re-attachable to said brackets.

11. The method of claim 1, wherein said model for a simulated desired aligned stage of a patient's mal-aligned teeth is an electronic model, and said inter-bracket distances are determined by software.

12. A method of producing a customized arch wire device for orthodontic alignment of teeth, said method comprising:
   obtaining a model of a patient's mal-aligned teeth, said model having a plurality of teeth surfaces;

attaching a plurality of brackets to said teeth surfaces, each bracket having a width and a wire slot to accommodate said arch wire;

wherein adjacent brackets are spaced apart by a plurality of inter-bracket distances;

determining how said brackets move from their mal-aligned position to their aligned position in a simulated desired aligned stage of said patient's teeth;

obtaining an arch wire device comprising a customized wire length;

outside a patient's mouth, positioning said customized arch wire device into a geometric form that corresponds to the position and orientation of said plurality of brackets on said teeth surfaces in said simulated desired aligned stage;

wherein said customized arch wire device's length is comprised of a combined width of said brackets and combined inter-bracket distances between each set of adjacent brackets;

wherein said customized arch wire device further comprises multi-dimensional bends such that said customized arch wire device passes passively through each bracket affixed to said teeth surfaces of said simulated desired aligned stage;

wherein said arch wire is configured to be capable being completely detachable and re-attachable to said brackets;

wherein said multi-dimensional bends are further configured so that when a corresponding plurality of brackets are affixed in said patient's mouth at the same position and orientation as in said model, and said customized arch wire device is secured in place in said wire slots of said plurality of brackets with ties, clips, stops, adhesive or a combination of these, there is minimal movement between said customized arch wire device and said plurality of brackets;

wherein each said inter-bracket distance is configured to be the greater of:

A) a length of said customized arch wire device between adjacent brackets in said model of said patient's mal-aligned teeth, or B) the length of said customized arch wire device between adjacent brackets in said model for a simulated desired aligned stage.

13. The method as described in claim 12, wherein if said inter-bracket distance is smaller in said model for a simulated desired aligned stage than said inter-bracket distance is in said model of said patient's mal-aligned teeth, then;

further configuring a corresponding portion of said arch wire to consist of curves and bends such that the distance between said brackets, when said arch wire is in a passive or recoiled state, is reduced to the length of said inter-bracket distance for said models for a simulated desired aligned stage.

* * * * *